US011443149B2

(12) United States Patent
Francois et al.

(10) Patent No.: US 11,443,149 B2
(45) Date of Patent: Sep. 13, 2022

(54) CUTTINGS IMAGING FOR DETERMINING GEOLOGICAL PROPERTIES

(71) Applicant: Schlumberger Technology Corporation, Sugar Land, TX (US)

(72) Inventors: Matthias Francois, Clamart (FR); Youssef Tamaazousti, Clamart (FR); Josselin Kherroubi, Clarmart (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 17/067,806

(22) Filed: Oct. 12, 2020

(65) Prior Publication Data
US 2021/0319257 A1    Oct. 14, 2021

Related U.S. Application Data

(60) Provisional application No. 63/009,599, filed on Apr. 14, 2020.

(51) Int. Cl.
| | |
|---|---|
| *G06K 9/62* | (2022.01) |
| *G01N 15/08* | (2006.01) |
| *G01N 21/25* | (2006.01) |
| *G01N 33/24* | (2006.01) |
| *G06V 10/147* | (2022.01) |

(52) U.S. Cl.
CPC ............ *G06K 9/627* (2013.01); *G01N 15/088* (2013.01); *G01N 21/255* (2013.01); *G01N 33/24* (2013.01); *G06K 9/628* (2013.01); *G06K 9/6256* (2013.01); *G06V 10/147* (2022.01)

(58) Field of Classification Search
CPC ........................... E21B 49/005; G01N 23/046
See application file for complete search history.

(56) References Cited

U.S. PATENT DOCUMENTS

| | | |
|---|---|---|
| 2010/0128932 A1 | 5/2010 | Dvorkin et al. |
| 2014/0149041 A1 | 5/2014 | Sung et al. |
| (Continued) | | |

OTHER PUBLICATIONS

Ran et al., "Rock Classification from Field Image Patches Analyzed Using a Deep Convolutional Neural Network," Aug. 18, 2019. (Year: 2019).*

(Continued)

*Primary Examiner* — Ross Varndell
(74) *Attorney, Agent, or Firm* — Jeffrey D. Frantz (57) ABSTRACT

Apparatus and methods for ascribing one of multiple predetermined sub-classes to multiple pixels of an image of an unknown rock sample retrieved from a geological formation. The ascription utilizes a deep learning model trained with an annotated training dataset. The annotated training dataset includes multi-pixel images of known rock samples and, for each known rock sample image, which sub-class corresponds to at least a subset of pixels of that image. For each pixel of the unknown rock sample image having an ascribed sub-class, which one of predetermined meta-classes is associated with that pixel is derived based on the sub-class ascribed to that pixel. The meta-classes represent different predetermined rock types. At least one property of the formation is predicted utilizing the ascription-derived meta-classes, including which rock type(s) are present in the formation.

20 Claims, 7 Drawing Sheets

(56) References Cited

U.S. PATENT DOCUMENTS

2016/0370274 A1  12/2016  Rowe et al.
2017/0200290 A1   7/2017  Bhattiprolu et al.
2020/0225177 A1*  7/2020  Sungkorn ............ G01V 11/002

OTHER PUBLICATIONS

Ran, X. et al., "Rock Classification from Field Image Patches Analyzed Using a Deep Convolutional Neural Network", Mathematics, 2019, 7(8), 755, 16 pages.

Xu, C. et al., "When Petrophysics Meets Big Data: What can Machine Do?", SPE195068-MS, 2019, presented at the SPE Middle East Oil and Gas Show and Conference, pp. 4, 12.

Extended European Search Report issued in European Patent Application No. 20201353.8 dated Mar. 31, 2021, 10 pages.

Cheng, G. et al., "Rock images classification by using deep convolution neural network", Journal of Physics: Conference Series 887, 2017, 6 pages.

Kathrada, M. et al., "Visual Recognition of Drill Cuttings Lithologies Using Convolutional Neural Networks to Aid Reservoir Characterisation", 2019 Reservoir Characterisation and Simulation Conference and Exhibition, Abu Dhabi, UAE, Sep. 17-19, 2019, 11 pages.

Girard, J. et al., "Learning Finer-class Networks for Universal Representations", British Machine Vision Conference (BMVC), 2018, 19 pages.

Equinor, "15FORCE Wade Deep Leaarining on Cutting Images—Computer Vision for Geoscience Interpretation" Youtube Video (see on Youtube: https://www.youtube.com/watch?v=Wh6PO9qxA5I), Oct. 1, 2018, Length of Video 18:18.

* cited by examiner

CUTTINGS IMAGING FOR DETERMINING GEOLOGICAL PROPERTIES

CROSS-REFERENCE TO RELATED APPLICATIONS

This application claims priority to and the benefit of U.S. Provisional Application No. 63/009,599, titled "A method and system for determining at least a property of a geological formation based on an rock sample image," filed Apr. 14, 2020, the entire disclosure of which is hereby incorporated herein by reference.

BACKGROUND OF THE DISCLOSURE

Surface logging is a wellsite service providing early indications about drilled rocks and reservoir potential. For example, a wellsite operator, known as a "mud logger," may attempt to perform lithology identification from drill cuttings returning from a well in order to reconstruct a geology map of the well. The mud logger creates a manual description based on images and acid tests. For each sample, the mud logger may examine cutting samples (e.g., through binoculars or other magnifying means) and attempt to recognize different rock types in the samples. If the rock types are not visually clear, some of the cuttings may be isolated for acid tests and final identification. The mud logger then attempts to quantify proportions of the different rock types from the samples. Using this information, a reconstruction of the well formation can be performed to create a lithology column. However, manual rock type identification and quantification can be very subjective (e.g., biased by the mud logger's geological background) and significantly time-consuming.

SUMMARY OF THE DISCLOSURE

This summary is provided to introduce a selection of concepts that are further described below in the detailed description. This summary is not intended to identify indispensable features of the claimed subject matter, nor is it intended for use as an aid in limiting the scope of the claimed subject matter.

The present disclosure introduces a method including ascribing one of multiple predetermined sub-classes to each of multiple pixels of an image of an unknown rock sample ("unknown rock sample image") retrieved from a geological formation. The ascription utilizes a deep learning model that is trained with an annotated training dataset. The annotated training dataset includes multiple multi-pixel images of known rock samples ("known rock sample images") and, for each known rock sample image, which of the sub-classes corresponds to at least a subset of pixels of that image. The method also includes deriving, for each pixel of the unknown rock sample image having an ascribed sub-class, which one of multiple predetermined meta-classes is associated with that pixel based on the sub-class ascribed to that pixel. The meta-classes are each representative of a different one of multiple predetermined rock types. The method also includes predicting at least one property of the geological formation utilizing the ascription-derived meta-classes. Predicting the at least one property includes predicting which one or more of the rock types are present in the geologic formation.

The present disclosure also introduces an apparatus including a processing system having a processor and a memory storing an executable computer program code. By executing the computer program code, the processor ascribes one of multiple predetermined sub-classes to each of multiple pixels of an image of an unknown rock sample ("unknown rock sample image") retrieved from a geological formation. The ascription utilizes a deep learning model that is stored in the memory and that was trained with an annotated training dataset. The annotated training dataset includes multi-pixel images of known rock samples ("known rock sample images") and, for each known rock sample image, which of the sub-classes corresponds to at least a subset of pixels of that image. By executing the computer program code, the processor also derives, for each pixel of the unknown rock sample image having an ascribed sub-class, which one of multiple predetermined meta-classes is associated with that pixel based on the sub-class ascribed to that pixel. The meta-classes are each representative of a different one of multiple predetermined rock types. By executing the computer program code, the processor also predicts at least one property of the geological formation utilizing the ascription-derived meta-classes. The at least one property includes which one or more of the rock types are present in the geologic formation. The apparatus may further include an imaging device for obtaining the unknown rock sample image.

The present disclosure also introduces a non-transitory, tangible, computer-readable medium having stored thereon computer-readable instructions executable by a processing system for ascribing one of multiple predetermined sub-classes to each of multiple pixels of an image of an unknown rock sample ("unknown rock sample image") retrieved from a geological formation. The ascription utilizes a deep learning model that is trained with an annotated training dataset. The annotated training dataset includes multi-pixel images of known rock samples ("known rock sample images") and, for each known rock sample image, which of the sub-classes corresponds to at least a subset of pixels of that image. The computer-readable instructions also executable by the processing system for deriving, for each pixel of the unknown rock sample image having an ascribed sub-class, which one of multiple predetermined meta-classes is associated with that pixel based on the sub-class ascribed to that pixel. The meta-classes are each representative of a different one of multiple predetermined rock types. The computer-readable instructions also executable by the processing system for predicting at least one property of the geological formation utilizing the ascription-derived meta-classes. The at least one property includes predicting which one or more of the rock types are present in the geologic formation.

These and additional aspects of the present disclosure are set forth in the description that follows, and/or may be learned by a person having ordinary skill in the art by reading the material herein and/or practicing the principles described herein. At least some aspects of the present disclosure may be achieved via means recited in the attached claims.

BRIEF DESCRIPTION OF THE DRAWINGS

The present disclosure is understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for simplicity and clarity and does not in itself dictate a relationship between the various embodiments and/or configurations discussed.

With the rise of image datasets in recent years, as well as advances in machine learning (ML), attempts have been made to perform rock identification utilizing machine learning. Such attempts have included performing classification, using deep convolution neural network analysis, of thin sections of cuttings from oilfield rock images and of drilling cuttings. A common aspect of these works is that they formalized the task of automatic cuttings recognition as a classification of each sample. That is, just one class (the most present rock type) is assigned to each cuttings image. Accordingly, these attempts did not permit precise analysis of cutting mixtures, where more than one rock type is present in the images, such as appear during transition from one lithology to another during drilling. Moreover, the prior attempts also did not permit determining the proportion of rock types, which is utilized for interpreted lithology, such as for reconstruction and reordering of geological layers.

The present disclosure introduces one or more aspects pertaining to performing mud logger tasks semiautomatically or automatically, such as with artificial intelligence, and in a manner that may resolve the shortcomings of the attempts described above. For example, the present disclosure introduces one or more aspects related to segmentation (i.e., pixel-level classification) that provides finer automated descriptions that may be utilized for the identification of mixtures of rock types and their quantification (e.g., by proportion). A convolutional neural network is trained to perform cuttings segmentation, such as to classify each pixel in a cuttings image. The model is trained on a dataset of cutting sample images collected from lithologies around the world and manually annotated at the pixel-level (i.e., assigning a rock type to each image pixel). Moreover, because rock types are assessed at the pixel-level, a proportion of each rock type can be estimated so as to quantify each rock type in the image. The model may be learned in a transfer learning scenario. For example, an existing model that was pretrained for another purpose, such as on a large generic set of natural images, may be fine-tuned for the current application, such as via modification and training with drilling cuttings images. The model may be designed to perform a multi-scale processing, such as including processing different scales of objects, in order to handle multiple grain sizes of cuttings.

Figure 1:
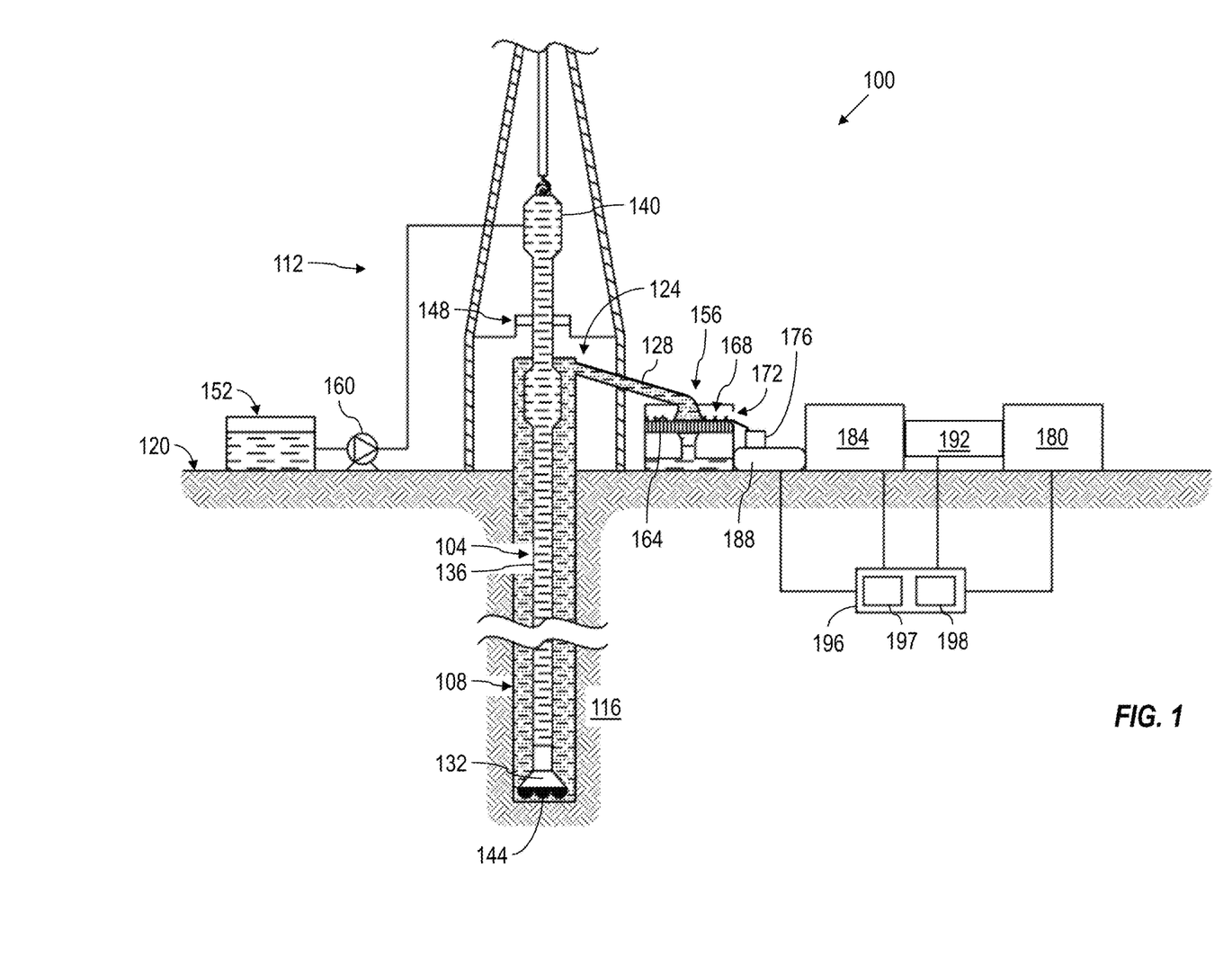
FIG. 1 is a schematic view of at least a portion of an example implementation of a wellsite installation according to one or more aspects of the present disclosure.

FIG. 1 is a schematic view of at least a portion of an example implementation of an installation 100 for drilling a borehole for an oil/gas well at a wellsite according to one or more aspects of the present disclosure. The installation 100 comprises a rotary drilling tool 104, for drilling a wellbore (cavity) 108, as well as a surface installation 112 where drilling pipes are placed in the wellbore 108. The wellbore 108 is formed in a geologic formation (substratum) 116 by the rotary drilling tool 104. At the wellsite surface 120, a well head 124 having a discharge pipe 128 closes the wellbore 108.

The drilling tool 104 comprises a drilling head 132, a drill string 136, and a liquid injection head 140. The drilling head 132 comprises a drill bit 144 for drilling through the rocks of the geologic formation 116. The drill string 136 is formed by a set of hollow drilling pipes through which drilling fluid is pumped from the surface 120 to the drilling head 132 via the liquid injection head 140. The drilling fluid is a drilling mud, such as a water-based or oil-based drilling mud.

The surface installation 112 comprises a support (e.g., a top drive) 148 for supporting the drilling tool 104 and driving it in rotation, an injector 152 for injecting the drilling fluid, and a shale shaker 156. The injector 152 is hydraulically connected to the injection head 140 in order to introduce and pump (e.g., via one or more pumps 160) the drilling fluid into the drill string 136. The shale shaker 156 collects the drilling fluid, charged with drilling cuttings, flowing out from the discharge pipe 128. The shale shaker 156 comprises a sieve 164 allowing the separation of the solid drilling cuttings 168 from the drilling mud. The shale shaker 156 also comprises an outlet 172 for evacuating the drilling cuttings 168.

One or more aspects of the present disclosure relate to methods and systems for analyzing the cuttings 168. Such systems may be situated at the wellsite, such as in the vicinity of the shale shaker 156, as depicted in FIG. 1, or in a cabin or other facility a few hectometers from the shale shaker 156. Such systems may instead be situated away from the wellsite, such as in a laboratory.

The example of such systems depicted in FIG. 1 comprises a container or other sampler 176 for collecting the cuttings 168 discharged from the outlet 172. An imaging device 180 for taking one or more multi-pixel images of a sample of the cuttings 168. Such sample is referred to herein as the unknown rock sample, in that the imaging device 180 (and other components) is used to identify or otherwise predict one or more properties of the geologic formation 116 via automatic analysis of the image of the unknown rock sample generated by the imaging device 180. The imaging device 180 may be or comprise an optical or electronic microscope or a camera.

The system may also comprise a preparation unit 184, such as may wash, dry, separate, and/or otherwise prepare the sampled cuttings 168 prior to imaging. However, the preparation unit 184 is optional, or perhaps able to be bypassed, such that cuttings 168 may be imaged just after having been sampled. It is to be noted that the cuttings 168 may not be separated from each other before being imaged by the imaging device 180.

The unknown rock sample may be automatically sampled, including being transferred to the preparation device 184

(when utilized) and then to imaging device 180 via a conveyor 188 and a transport device 192. The preparation and/or imaging may be performed automatically via various devices commanded via a sequence of actions of the preparation device 184 and the imaging device 180, among others. However, other conveyance devices may also or instead be used for transporting the cuttings 168. Furthermore, the sampling and conveyance of the cuttings 168 to the imaging device 180 may be performed manually in some embodiments.

The system also comprises a processing system 196 connected to at least the imaging device 180 in order to receive images taken by the imaging device 180. The processing system 196 may be or comprise at least a portion of one or more instances of the processing system 700 described below with respect to FIG. 11. The processing system 196 may comprise an analysis module 197 operable to analyze the image taken by the imaging device 180, as described below. The processing system 196 may also, such as in implementations in which the sampling and/or conveyance and/or preparation and/or imaging are automatic, comprise a control unit 198 for controlling the preparation and imaging of the sample. In such implementations, among others within the scope of the present disclosure, the processing system 196 may also able to communicate with the conveyor 188, the preparation device 185, the transport device 192, and the imaging device 180. The processing system 196 may also communicate with other modules at the wellsite, such as to determine the depth from which unknown rock samples are retrieved, perhaps via known or future-developed processes (e.g., based on lag time). The processing system 196 may be situated in the vicinity of the imaging device 180, or remotely from the imaging device 180. The processing system 196 may also comprise several modules situated at different locations, such as one situated in the vicinity of the imaging device 180 and one situated remotely from the imaging device 180. Each such module may be or comprise at least a portion of the processing system 700 described below with respect to FIG. 11.

It is to be noted that the system depicted to FIG. 1 is an exemplary implementation. It has been described when the unknown rock sample is a sample of cuttings that is automatically handled. However, in other implementations within the scope of the present disclosure, the sample may be manually collected, transferred by an operator to a cabin or to a lab, at which the sample may be imaged and optionally prepared. Implementations of systems within the scope of the present disclosure may also comprise just the imaging device 180 and the processing system 196. Such system may be utilized to, for example, analyze drill cuttings and/or other types of rock samples.

Figure 2:
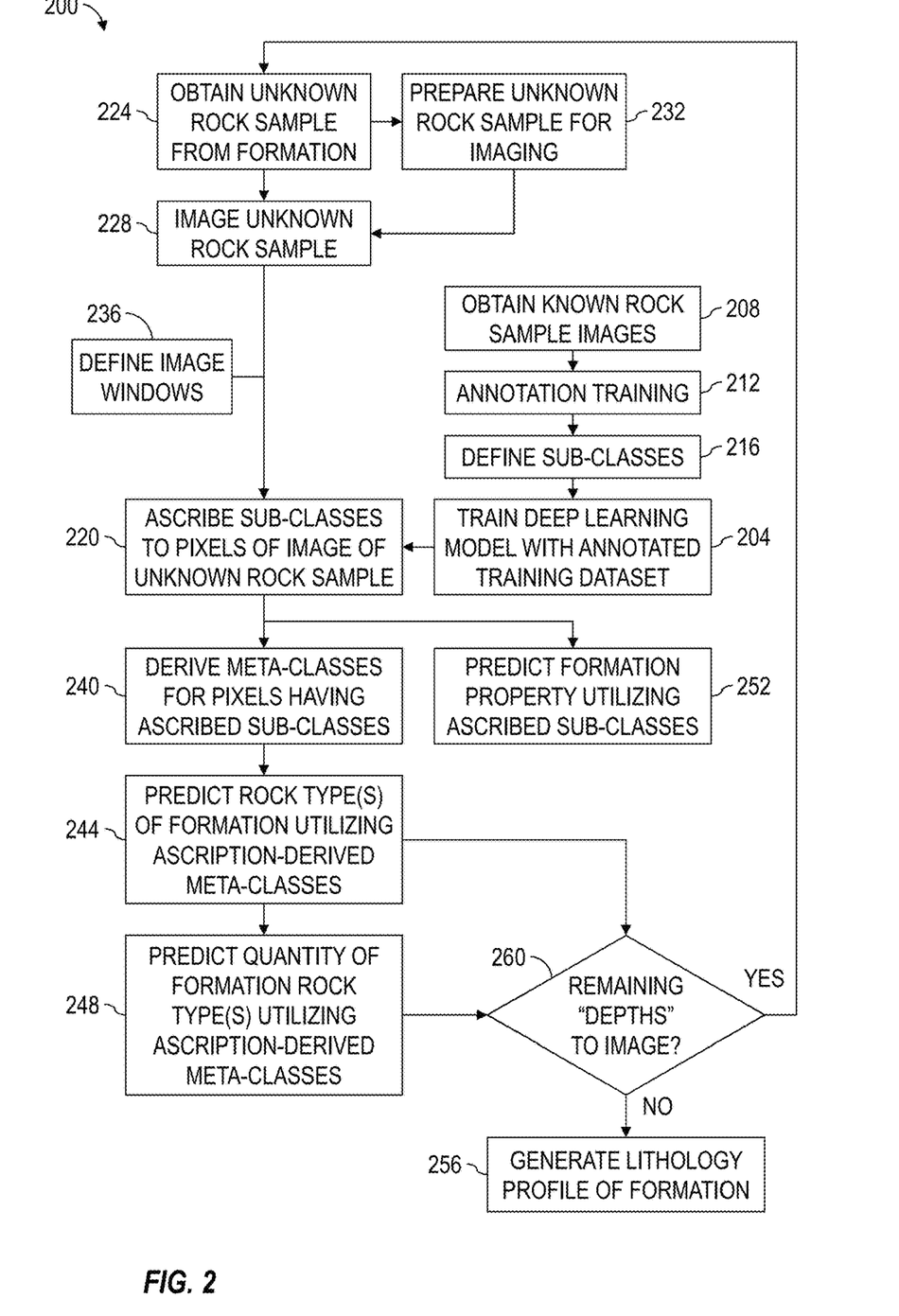
FIG. 2 is a flow-chart diagram of at least a portion of an example implementation of a method according to one or more aspects of the present disclosure.

FIG. 2 is a flow-chart diagram of at least a portion of an implementation of a method 200 according to one or more aspects of the present disclosure. The method 200 pertains to using a multi-pixel image of a sample of the drill cuttings 168 ("unknown rock sample") as an input for predicting one or more properties of the sample as an output, via utilization of a model stored in a processing system, such as the processing system 196. One or more aspects of the method 200 may be utilized to perform automated rock type identification and quantification from images of cuttings captured by a given imager, such as the imaging device 180 and/or others.

Figure 3:
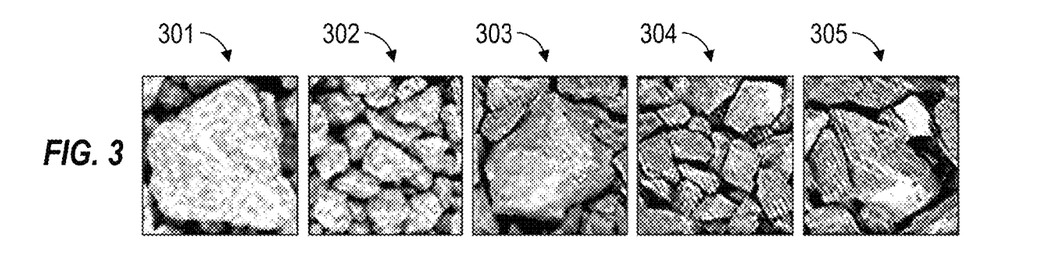
FIGS. 3 and 4 contain grayscale renderings of photos of rock samples pertaining to one or more aspects of the present disclosure.
Figures 4, 5:
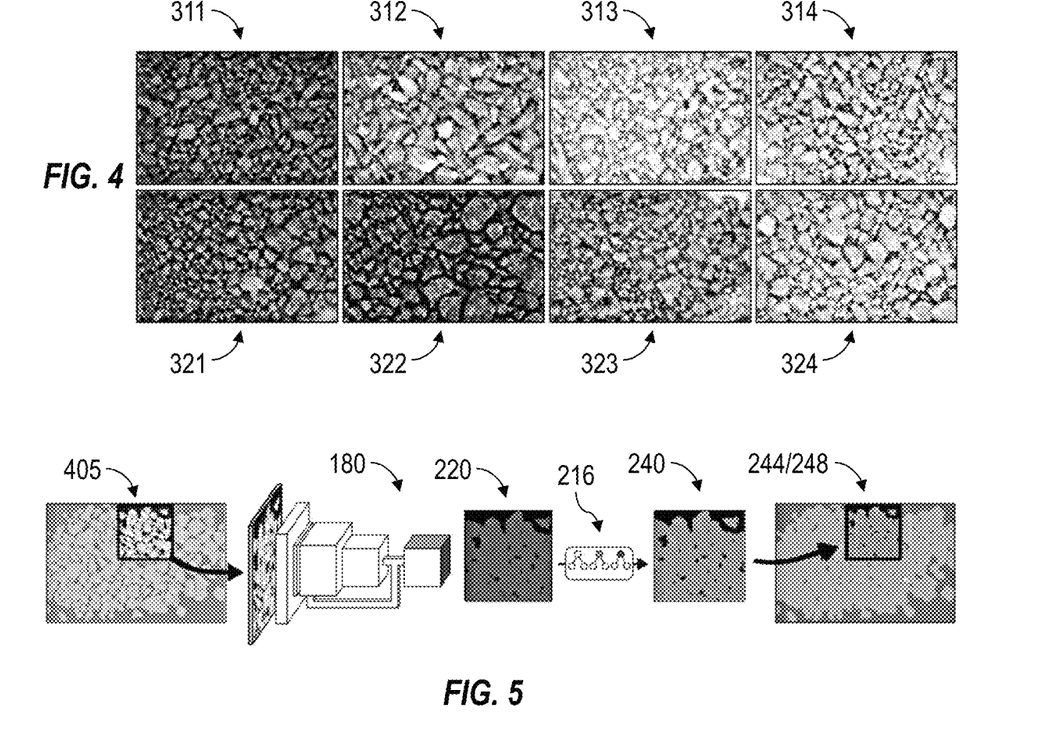
FIG. 5 is a flow diagram of at least a portion of an example implementation of a workflow according to one or more aspects of the present disclosure.

A challenge in cuttings recognition is the very high intra-class and very low inter-class variances. For example, cuttings of the same category come in a wide variety of shapes, textures, colors, orientations, size, and illuminations. Moreover, cuttings of two different categories might be very similar in terms of color and texture. FIG. 3 is presented as an example of intra-class variations of illuminations, sizes, and orientations in chunks from two example sandstone (i.e., a first category) samples 301, 302 and three example shale (i.e., a second category) samples 303-305, illustrating that it may be challenging to discriminate the categories from different classes based solely on visual criteria. FIG. 4 is presented as an example of intra-class and inter-class variations in terms of colors (shown in grayscale) of cuttings in four example shale samples 311-314 and four example carbonate samples 321-324. Samples from different categories may also have very similar colors. Thus, one or more aspects of the deep learning model introduced herein pertain to being able to capture the texture of the cuttings, including grain shape, grain size, etc., instead of just capturing their color. Moreover, especially during transition between different lithologies as the wellbore continues to be extended, the rock samples analyzed at the wellsite surface may include just one rock type or multiple rock types.

The present disclosure introduces a deep learning approach in which unknown rock sample images are input and, via the deep learning model, rock type is output at the pixel level. This corresponds formally to a segmentation task, where the model classifies the rock type of each pixel. This pixel-wise classification also permits straightforward relative rock quantification. That is, from the predictions output by the model, the proportion of cuttings of a given rock type in an imaged rock sample is estimated as the proportion of individual pixels in the image that were predicted as being that rock type. Moreover, the model is data-driven, and may thus handle the shape and color diversity aspects as the model is fed with more images of cuttings in different configurations.

Returning to FIG. 2, the method 200 may comprise training 204 the deep learning model with an annotated training data set (although some implementations of the method 200 within the scope of the present disclosure may not include the model training 204, such as when the model is already trained and available for use). For example, images of an appreciable number (e.g., greater than 100) of known rock samples of cuttings may be obtained 208. Obtaining 208 the known rock sample images may be performed in a standardized manner, such as by utilizing the same imaging device with the same settings (resolution, brightness, etc.), the same support tray or other background on which the known rock samples rest while being imaged, and the same focal distance from the imaging device to the support tray. The obtained 208 images may be of known rock samples of cuttings containing at least two rock types that are different with respect to geography, geology, and/or other factors. For example, the obtained 208 images may be of cuttings containing carbonate, sandstone, and shale. However, the obtained 208 images may include known rock samples that include more than three rock types, as well as other rock types not explicitly described herein, provided that the training dataset takes into account each of the rock types that are sought to be detected. Some of the obtained 208 images may also be of known rock samples that are dry, while other ones of the obtained 208 images may be of known rock samples that are wet. Some of the obtained 208 images may also be of known rock samples containing just one rock type, while other ones of the obtained 208 images may be of known rock samples containing a mixture of rock types. Thus, for example, the obtained 208 images may be of known rock samples having dry single lithologies, dry mixed lithologies, wet single lithologies, and wet mixed lithologies. A first portion of the obtained 208 images (e.g., 75 of the 100 obtained images) may be utilized for training the model, whereas a second portion of the obtained 208 images (e.g., the remaining 25 images) may be utilized for evaluating performance of the model.

Annotation training 212 may then be performed utilizing at least a subset of the obtained 208 images. For example, mud-logging experts (i.e., human personnel) may manually annotate the obtained 208 images. However, as segmentation task, a pixel-level delineation of each rock boundary in each of the obtained 208 images is a precise process and, thus, may be very time-consuming. In order to alleviate this, the annotation training 212 may utilize just the obtained 208 images of single lithology samples (i.e., images with cuttings of the same rock type). Moreover, the annotation training 212 may utilize an image-processing algorithm to detect and separate the image background from the cuttings and then derive per-pixel labels of the rock types in each pixel of each obtained 208 image.

Sub-classes of the rock type labels may then be defined 216. That is, because of the high/low intra/inter-class variances, training a model directly on just two or three classes (corresponding to each rock type) will result in a model that is inaccurate and unable to discern visually similar but different rock type cuttings. To avoid this visual appearance-based confusion, each of the classes are split into sub-classes. Such refinement may be based on various visual parameters, such as grain size, color, and porosity, among others. Each defined 216 sub-class is, thus, a child of one of the classes defined in the annotation training 212, forming a hierarchy. In other words, a sub-class is defined based solely on the rocks labeled as pertaining to a particular class, i.e., a set of different sub-classes is defined for each class. For this reason, the classes defined in the annotation training 212 are referred to as "meta-classes" to distinguish from the sub-classes. Each sub-class is hierarchically contained within one of the meta-classes. The number of defined 216 sub-classes may be 10, 20, or more times the number of meta-classes. However, other relative proportions of the meta-classes and sub-classes are also within the scope of the present disclosure. Defining 216 the sub-classes may be performed visually by a human being, but in order to at least partially automate and/or otherwise facilitate the process, may utilize known or future-developed computer-vision techniques to permit easier convergence of the model and/or techniques such as clustering of the rock samples associated to the class.

The deep learning model is then trained 204. For example, following a de-facto transfer-learning scenario, a residual neural network ("ResNet") model pre-trained on a database of images, such as the ImageNet database, may be adapted to the present segmentation task. ResNet is a convolutional neural network that consists in a stack of 2D-convolutional layers with identity shortcut connection ("skip") connections to handle multi-scale objects. For example, the last layers from the pre-trained ResNet model may be removed and replaced by a set of C filters of size 3×3, where C is the number of sub-classes, and then 2×2 max-pooling filters may be added between low-level layers to better handle cuttings with large grain size. Thus, each last-layer filter acts as a patch-based classifier on the input images (or on smaller windows of the input images) and gives a segmentation map of size H'×W', which may then be resampled bi-linearly to the input size H×W (e.g., 512×512 pixels per image). The model is trained 204 using a loss function. For example, the model may be trained 204 using the conventional, pixelwise, softmax cross-entropy loss function, in which the softmax function normalizes the output to a probability distribution, and the cross-entropy loss function indicates the distance between output distribution and the actual distribution. Here, again, just the single lithology samples may be used during this training 204.

The deep learning model has networks capable of unsupervised learning from data that is unstructured or unlabeled. The model may use a convolutional neural network (CNN) that is trained 204 (such as described above) using the annotated training dataset resulting from the meta-class annotation training 212 and sub-class definition 216. The training 204 may result in weight optimization of the nodes of network(s) of the model based on minimizing the loss function for the training dataset. In other words, the weights of each node of the model network(s) are tuned so that the model minimizes the errors when classifying the input images (or smaller windows thereof) of the training dataset.

The method 200 comprises ascribing 220 sub-classes to the pixels (or a subset thereof) of an image of an unknown rock sample. For example, the method 200 may also comprise obtaining 224 the unknown rock sample from a geologic formation via portions of the installation 100 depicted in FIG. 1. The obtained 224 sample is then imaged 228, such as by the imaging device 180 depicted in FIG. 1. Prior to such imaging 228, the obtained 224 sample may be prepared 232 for the imaging 228, whether via washing, drying, orienting, and/or otherwise, such as via operation of the preparation unit 184 depicted in FIG. 1. However, other means for obtaining the image of the unknown rock sample are also within the scope of the present disclosure.

Parameters of the unknown rock sample image resulting from the imaging 228 may be standardized parameters. For example, the standardized parameters may include settings of the imaging device 180, such as one or more of resolution, brightness, type of support on which the sample of drill cuttings rest during the imaging 228, and distance between the support and the imaging device 180 (e.g., focal distance). The standardized parameters may be the same (or substantially similar) to the parameters utilized to obtain 208 the known rock sample images.

The method 200 may also comprise defining 236 windows in the unknown rock sample image to split the image into smaller chunks that are used as input images into the trained model. The pixels (or a subset thereof) in each window are each ascribed 220 to one of the defined 216 sub-classes, resulting a segmentation map at the sub-class level as an output. The meta-class for each such pixel of that sub-class segmentation map is then derived 240 by mapping the ascribed sub-class of each pixel to the meta-class hierarchically containing that sub-class. This derivation 240 provides a prediction of the meta-class level, thus predicting 244 the rock type for each analyzed pixel of the input image. For example, if for at least a predetermined, substantial portion (e.g., 80%) of the pixels of the image, the derived 240 meta-classes are the same, that predicts 244 that the unknown rock sample belongs to that meta-class, and substantially comprises just the rock type annotated 212 to that meta-class. Alternatively, or additionally, if for a predetermined smaller portion (e.g., 20%) of the pixels of the image, the derived 240 meta-classes predict a first meta-class, and for another predetermined smaller portion (e.g., 20%) of the pixels of the image, the derived 240 meta-classes predict a second meta-class, that predicts 244 that the unknown rock sample comprises the two rock types annotated 212 to those two meta-classes.

The method 200 may also comprise predicting 248 the quantity of each predicted 244 rock type in the unknown rock sample. For example, such prediction 248 may be the result of a quantity or tally of pixels associated to each meta-class derived 240 from the ascribed 220 sub-classes. To continue akin to the examples in the immediately preceding paragraph, if 40% of the derived 240 meta-classes predict a first rock type and 60% of the derived 240 meta-classes predict a second rock type, then the quantity predicting 248 may be that the unknown rock sample comprises 40% of the first rock type and 60% of the second rock type.

The method 200 may also comprise predicting 252 one or more properties of the geologic formation utilizing the ascribed 220 sub-classes. For example, if a majority (or some other predetermined threshold) of the ascribed 220 sub-classes are for a specific value or range of grain size, color, porosity, or other geologic property, that may predict 252 the existence of that specific value or range for the property.

The method 200 may also comprise generating 256 a lithology profile of the geologic formation penetrated by the wellbore. In this case, cuttings (i.e., rock sample) are obtained and imaged for each depth and the quantity of rock type for each rock sample is predicted using the method described in relationship with FIG. 2. For generating 256 the lithology profile, the method 200 then includes, for example, if it is determined 260 that remaining depths have not yet been analyzed in the manner described above, the method 200 may revert to obtaining 224 another unknown rock sample corresponding to a depth for which a corresponding rock sample has not been analyzed (for example, the next depth for which a corresponding rock sample has not been analyzed), and the subsequent actions may be repeated. After unknown rock samples from each depth of intended investigation are analyzed, the rock type predictions 244, quantity predictions 248, formation property predictions 252, and perhaps other predictions may be arranged with respect to the corresponding depths from which each unknown rock sample was retrieved, thereby generating 256 the lithology profile. However, this may also be performed in substantial real-time, by adding the results of each new iteration of the method to an on-going lithology profile.

FIG. 5 is a schematic diagram of a portion 400 of the method 200 shown in FIG. 2. For example, a window 405 is defined 236 in an image of an unknown rock sample. The window 405 is examined by the imaging device 180 to ascribe 220 sub-classes separately to each pixel in the window. Meta-classes are then derived 240 from the ascribed 220 sub-classes based on the sub-class definitions 216. The derived 240 meta-classes are then tallied for the rock type prediction 244 and, perhaps, the rock type quantity prediction 248. When several windows in the image are created for being processed by the neural network, the windows in which the pixels have been associated to the meta-classes may be reassembled into the image before the rock type quantity prediction 248 is performed.

Figure 6:
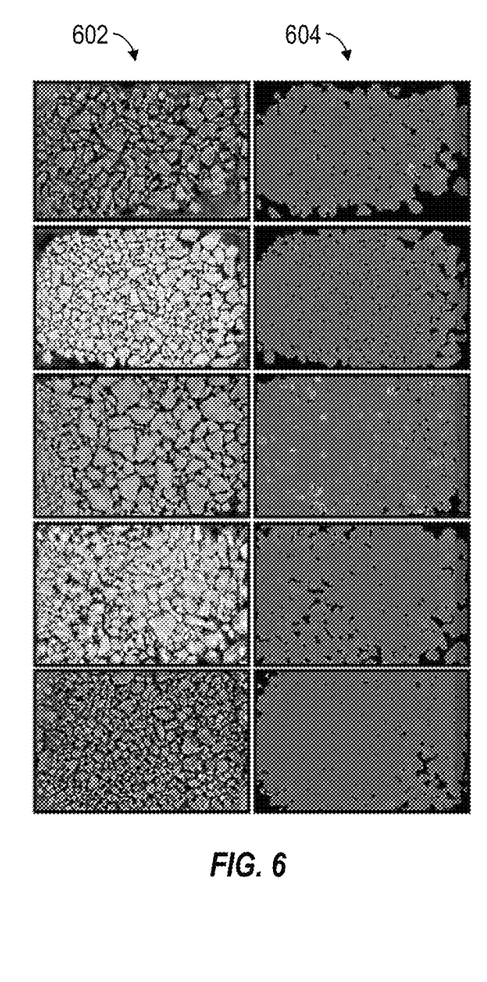
FIGS. 6-10 contain grayscale renderings of photos of example rock samples used for experimentation and example experimentation results pertaining to one or more aspects of the present disclosure.
Figure 7:
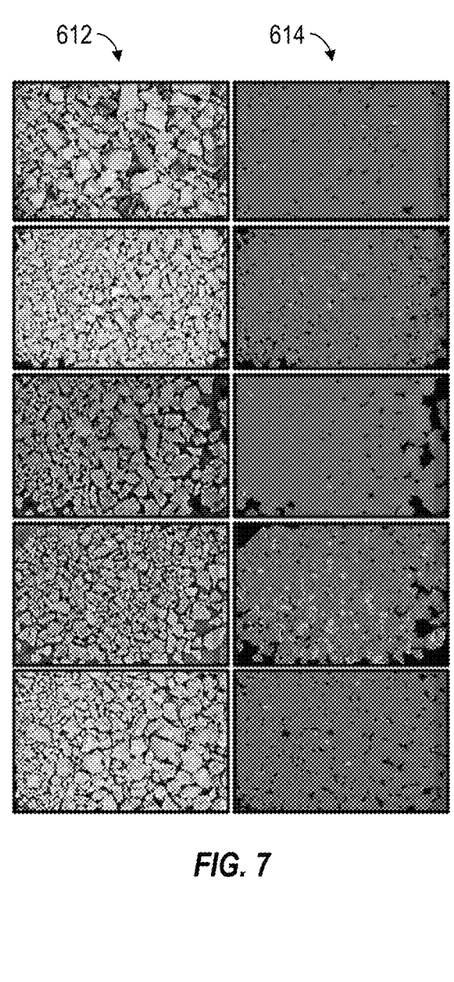
Figure 8:
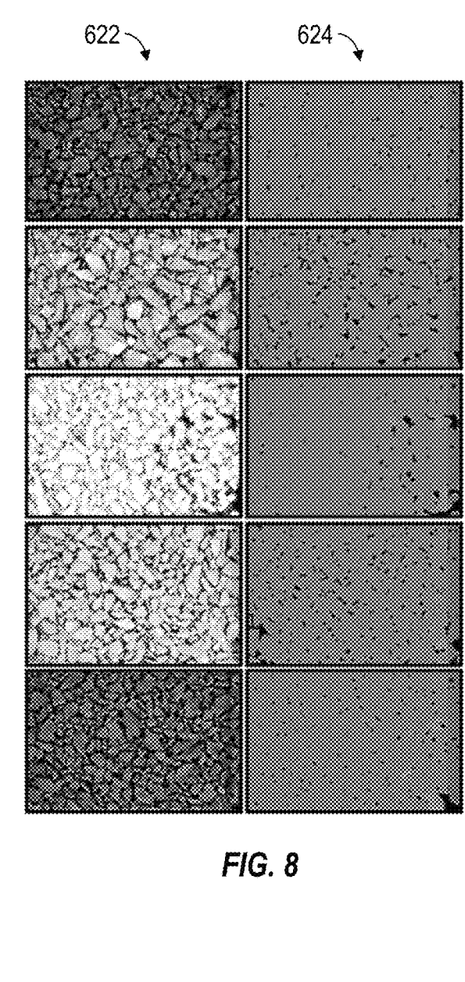

Aspects of the present disclosure have been tested by experimentation. For rock type identification, a pixel accuracy evaluation metric was used, while for rock type quantification, a proportion accuracy evaluation metric was used. Experimental results for single lithology images included a 94% accuracy for rock type identification and 98% accuracy for rock type quantification. FIG. 6 depicts example inputs 602 and qualitative results 604 for sandstone, FIG. 7 depicts example inputs 612 and qualitative results 614 for carbonate, and FIG. 8 depicts example inputs 622 and qualitative results 624 shale. For simplicity, ground-truths are not displayed.

Figure 9:
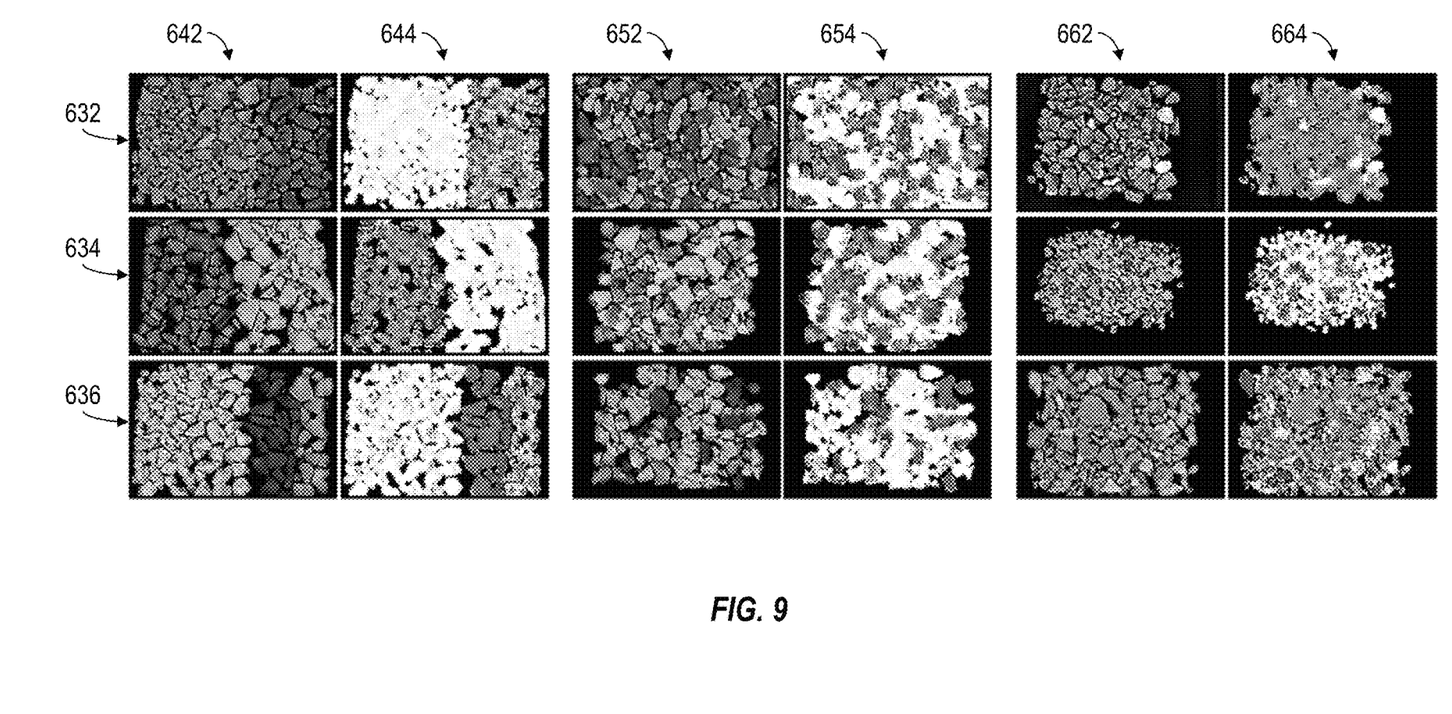

Experimental results for mixed lithology images included a 72% accuracy for rock type identification and 89% accuracy for rock type quantification. FIG. 9 depicts example inputs 642, 652, 662 and qualitative results 644, 654, 664 for mixtures of sandstone and carbonate cuttings in rows 632 and 634, as well as mixtures of sandstone, carbonate, and shale in row 636. The experimental results are from model that was trained on just pure lithologies and, thus, was not trained with lithology mixtures. The inputs 642 and results 644 depict a non-realistic, clean organization of cuttings. The inputs 652 and results 654 depict a more realistic setting with similar portions of each rock type present in the image. The inputs 662 and results 664 depict a more frequent and complex case were some residuals of cuttings from other rock types appears in a big portion of a certain rock type. While some insignificant errors might appear, the model is globally quite accurate in terms of identification and localization of the different cuttings in the three different settings.

Note that here, the mixtures at the pixel-level for the evaluation are labelled. As expected, the results are lower (~20% drop compared to single lithology), but it is clear that the model handled a very different configuration that what was used for training. Thus, by training with just single lithology data, which is much easier to annotate than mixed lithology images, the model is nonetheless adept at automatic rock type identification and quantification of mixed lithology samples. Nonetheless, also utilizing mixed lithology images for training is also possible, and further improves results.

Figure 10:
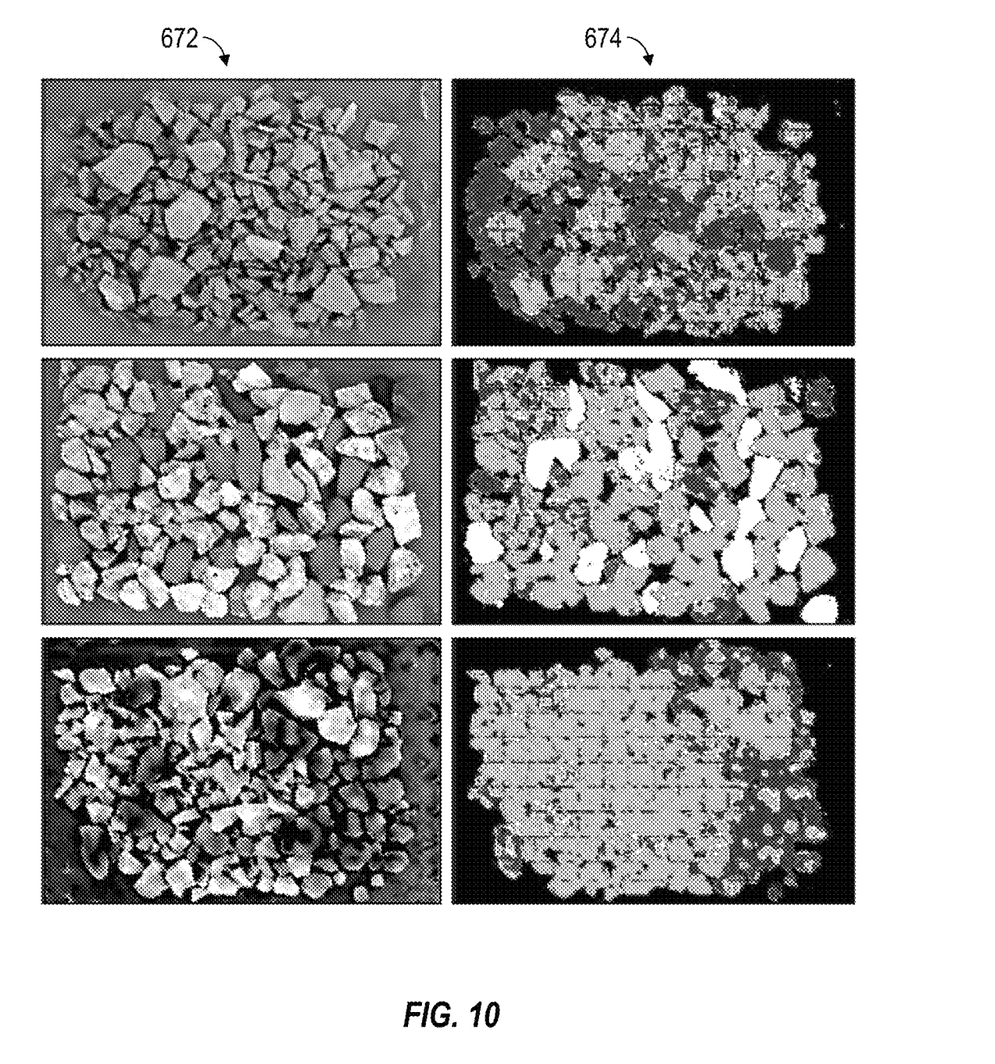

In the operational workflow of cuttings identification and quantification, the process of drying the originally wet cuttings is time consuming. Experimental results 674 with images of wet cuttings as inputs 672 are depicted in FIG. 10, which shows that, despite the model having been trained on dry single lithology images, it nonetheless performs relatively well with wet mixed lithologies. Of course, the efficiency of the model may be increased by training the model based on dry as well as wet cuttings images and/or known rock samples in different configurations.

Figure 11:
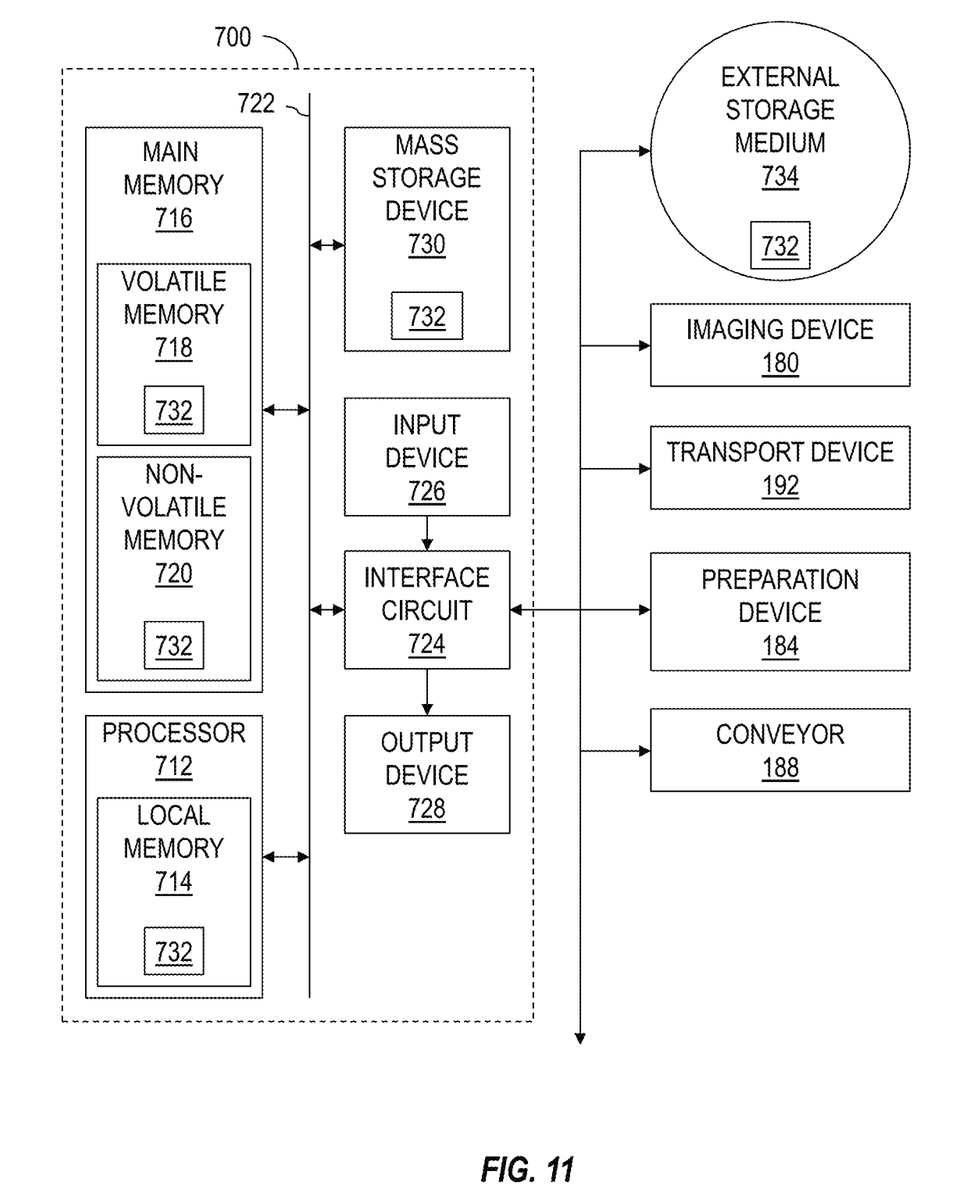
FIG. 11 is a schematic view of at least a portion of an example implementation of a processing system according to one or more aspects of the present disclosure.

FIG. 11 is a schematic view of at least a portion of an example implementation of a processing system 700 according to one or more aspects of the present disclosure. The processing system 700 may be or form at least a portion of one or more equipment controllers, processors, processing systems, and/or other electronic devices shown in (or otherwise associated with) FIG. 1 and/or FIG. 5, including for performing at least a portion of the method 200 shown in FIG. 2. Accordingly, the following description refers to FIGS. 1, 2, 5, and 11, collectively.

The processing system 700 may be or comprise, for example, one or more processors, controllers, special-purpose computing devices, personal computers (PCs, e.g., desktop, laptop, and/or tablet computers), personal digital assistants, smartphones, industrial PCs (IPCs), programmable logic controllers (PLCs), servers, internet appliances, and/or other types of computing devices. The processing system 700 may be or form at least a portion of the analysis module 197, the control unit 198, other components of the processing system 196, and/or the processing system 196 itself. Although it is possible that the entirety of the processing system 700 is implemented within one device, it is also contemplated that one or more components or functions of the processing system 700 may be implemented across multiple devices, some or an entirety of which may be at the wellsite and/or remote from the wellsite.

The processing system 700 may comprise a processor 712, such as a general-purpose programmable processor.

The processor 712 may comprise a local memory 714 and may execute computer/machine-readable and executable program code instructions 732 (i.e., computer program code) present in the local memory 714 and/or another memory device. The processor 712 may be, comprise, or be implemented by one or more processors of various types suitable to the local application environment, and may include one or more of general-purpose computers, special-purpose computers, microprocessors, digital signal processors (DSPs), field-programmable gate arrays (FPGAs), application-specific integrated circuits (ASICs), and processors based on a multi-core processor architecture, as non-limiting examples. Examples of the processor 712 include one or more INTEL microprocessors, microcontrollers from the ARM and/or PICO families of microcontrollers, and embedded soft/hard processors in one or more FPGAs.

The processor 712 may execute, among other things, the program code instructions 732 and/or other instructions and/or programs to implement the example methods and/or operations described herein. For example, the program code instructions 732, when executed by the processor 712 of the processing system 700, may cause the processor 712 to receive and process sensor data, such as unknown rock sample images obtained 228 by the imaging device 180. The program code instructions 732, when executed by the processor 712 of the processing system 700, may also or instead cause the processor 712 to output control data (i.e., control commands) to cause one or more portions or pieces of wellsite equipment, such as the imaging device 180, the preparation device 184, the conveyor 188, and/or the transport device 192, perhaps including to perform one or more aspects of the example methods and/or operations described herein.

The processor 712 may be in communication with a main memory 716, such as may include a volatile memory 718 and a non-volatile memory 720, perhaps via a bus 722 and/or other communication means. The volatile memory 718 may be, comprise, or be implemented by random access memory (RAM), static RAM (SRAM), dynamic RAM (DRAM), synchronous DRAM (SDRAM), RAMBUS DRAM (RDRAM), and/or other types of RAM devices. The non-volatile memory 720 may be, comprise, or be implemented by read-only memory, flash memory, and/or other types of memory devices. One or more memory controllers (not shown) may control access to the volatile memory 718 and/or non-volatile memory 720.

The processing system 700 may also comprise an interface circuit 724, which is in communication with the processor 712, such as via the bus 722. The interface circuit 724 may be, comprise, or be implemented by various types of standard interfaces, such as an Ethernet interface, a universal serial bus (USB), a third-generation input/output (3GIO) interface, a wireless interface, a cellular interface, and/or a satellite interface, among others. The interface circuit 724 may comprise a graphics driver card. The interface circuit 724 may comprise a communication device, such as a modem or network interface card to facilitate exchange of data with external computing devices via a wide area network (WAN, e.g., an Ethernet connection, a DSL, a telephone line, a coaxial cable, a cellular telephone system, a satellite communication system, etc.).

The processing system 700 may be in communication with various sensors, video cameras, actuators, processing devices, equipment controllers, and other devices of the well construction system via the interface circuit 724, perhaps including the imaging device 180, the preparation device 184, the conveyor 188, and/or the transport device 192. The interface circuit 724 can facilitate communications between the processing system 700 and one or more devices by utilizing one or more communication protocols, such as an Ethernet-based network protocol (e.g., ProfiNET, OPC, OPC/UA, Modbus TCP/IP, EtherCAT, UDP multicast, Siemens S7 communication, etc.), a proprietary communication protocol, and/or another communication protocol.

One or more input devices 726 may also be connected to the interface circuit 724. The input devices 726 may permit a human user to enter the program code instructions 732, which may be or comprise control data, operational parameters, operational set-points, a well construction plan, and/or a database of operational sequences. The program code instructions 732 may further comprise modeling or predictive routines, equations, algorithms, processes, applications, and/or other programs operable to perform example methods and/or operations described herein. For example, the program code instructions 732 may comprise the trained 204 deep learning model. The input devices 726 may be, comprise, or be implemented by a keyboard, a mouse, a joystick, a touchscreen, a trackpad, a trackball, an isopoint, and/or a voice recognition system, among other examples. One or more output devices 728 may also be connected to the interface circuit 724. The output devices 728 may permit for visualization or other sensory perception of various data, such as sensor data, status data, and/or other example data. The output devices 728 may be, comprise, or be implemented by video output devices (e.g., a liquid crystal display (LCD), a light-emitting diode (LED) display, a cathode ray tube (CRT) display, a touchscreen, etc.), printers, and/or speakers, among other examples.

The processing system 700 may comprise a mass storage device 730 for storing data and program code instructions 732. The mass storage device 730 may be connected to the processor 712, such as via the bus 722. The mass storage device 730 may be or comprise a tangible, non-transitory, computer-readable storage medium, such as a floppy disk drive, a hard disk drive, a compact disk (CD) drive, and/or digital versatile disk (DVD) drive, among other examples.

The processing system 700 may be communicatively connected with an external storage medium 734 via the interface circuit 724. The external storage medium 734 may be or comprise a removable storage medium (e.g., a CD or DVD), such as may be operable to store data and program code instructions 732.

As described above, the program code instructions 732 may be stored in the mass storage device 730, the main memory 716, the local memory 714, and/or the removable storage medium 734. Thus, the processing system 700 may be implemented in accordance with hardware (perhaps implemented in one or more chips including an integrated circuit, such as an ASIC), or may be implemented as software or firmware for execution by the processor 712. In the case of firmware or software, the implementation may be provided as a computer program product including a non-transitory, computer-readable medium or storage structure storing computer program code instructions 732 (i.e., software or firmware) for execution by the processor 712. The program code instructions 732 may include program instructions or computer program code that, when executed by the processor 712, may perform and/or cause performance of one or more aspects of the methods, processes, and/or operations described herein.

In view of the entirety of the present disclosure, including the figures and the claims, a person having ordinary skill in the art will readily recognize that the present disclosure introduces a method comprising: (A) ascribing one of a plurality of predetermined sub-classes to each of a plurality of pixels of an image of an unknown rock sample ("unknown rock sample image") retrieved from a geological formation, wherein: (1) the ascription utilizes a deep learning model that is trained with an annotated training dataset; and (2) the annotated training dataset comprises: (i) a plurality of multi-pixel images of known rock samples ("known rock sample images"); and (ii) for each known rock sample image, which of the sub-classes corresponds to at least a subset of pixels of that image; (B) for each pixel of the unknown rock sample image having an ascribed sub-class, deriving which one of a plurality of predetermined meta-classes is associated with that pixel based on the sub-class ascribed to that pixel, wherein the meta-classes are each representative of a different one of a plurality of predetermined rock types; and (C) predicting at least one property of the geological formation utilizing the ascription-derived meta-classes, wherein predicting the at least one property includes predicting which one or more of the rock types are present in the geologic formation.

Predicting the at least one property may further include predicting a quantity of each of the one or more rock types predicted to be present in the geologic formation.

The method may further comprise training the deep learning model with the annotated training dataset.

The deep learning model may include a convolutional neural network. In such implementations, among others within the scope of the present disclosure, the deep learning model may include nodes each associated with at least a weight, and the training may include optimizing the weights associated to each node using a loss function relative to the annotated training dataset. The deep learning model may have been defined using a transfer learning operation. The deep learning model may be based on a modified existing model, and the existing model may be trained on generic images.

The deep learning model may be defined to perform multi-scale processing.

The method may further comprise defining a plurality of windows in the unknown rock sample image, wherein each window may comprise a predetermined number of pixels and be of a predetermined shape. Each known rock sample image of the annotated training dataset may comprise the predetermined number of pixels and may be of the predetermined shape.

The method may further comprise forming the annotated training dataset, including: obtaining the known rock sample images, wherein the known rock samples depicted in the known rock sample images collectively include one or more known rock types; and defining each sub-class via association with at least one subset of pixels of a corresponding one or more of the known rock sample images. In such implementations, among others within the scope of the present disclosure, the method may further comprise associating each defined sub-class to one of the meta-classes that corresponds to the known rock type of the corresponding at least one subset of pixels. At least one of the known rock sample images may be an image of one of the known rock samples that comprises just one of the known rock types, and the at least one subset of pixels of that image may be associated with just one of the sub-classes.

Each sub-class may be representative of one or more rock properties. The one or more rock properties may include one or more of grain size, color, and porosity. The method may further comprise predicting one or more of grain size, color, and porosity of the geologic formation based on the ascriptions.

The known rock sample may comprise drill cuttings. In such implementations, among others within the scope of the present disclosure, the unknown rock sample may be one of a plurality of unknown rock samples each retrieved from a different depth in the geological formation and depicted in a corresponding one of a plurality of unknown rock sample images, and the method may further comprise: performing the sub-class ascription, the meta-class derivation, and the at least one property prediction utilizing each of a plurality of unknown rock sample images; and generating a lithology profile of the geologic formation versus depth based on the property predictions.

The method may comprise collecting a sample of drill cuttings retrieved from a wellbore while drilling into the formation to form the wellbore and, via operation of an imaging device, imaging the sample of drill cuttings to obtain the unknown rock sample image. Parameters of the unknown rock sample image may be standardized parameters. The standardized parameters may include settings of the imaging device operation, including one or more of resolution, brightness, type of support on which the sample of drill cuttings rest during the imaging, and distance between the support and the imaging device.

The present disclosure also introduces an apparatus comprising a processing system comprising a processor and a memory storing an executable computer program code that, when executed by the processor: (A) ascribes one of a plurality of predetermined sub-classes to each of a plurality of pixels of an image of an unknown rock sample ("unknown rock sample image") retrieved from a geological formation, wherein: (1) the ascription utilizes a deep learning model that is stored in the memory and that was trained with an annotated training dataset; and (2) the annotated training dataset comprises: (i) a plurality of multi-pixel images of known rock samples ("known rock sample images"); and (ii) for each known rock sample image, which of the sub-classes corresponds to at least a subset of pixels of that image; (B) for each pixel of the unknown rock sample image having an ascribed sub-class, derives which one of a plurality of predetermined meta-classes is associated with that pixel based on the sub-class ascribed to that pixel, wherein the meta-classes are each representative of a different one of a plurality of predetermined rock types; and (C) predicts at least one property of the geological formation utilizing the ascription-derived meta-classes, wherein the at least one property includes which one or more of the rock types are present in the geologic formation. The apparatus may further comprise an imaging device for obtaining the unknown rock sample image.

The present disclosure also introduces a non-transitory, tangible, computer-readable medium having stored thereon computer-readable instructions executable by a processing system for: (A) ascribing one of a plurality of predetermined sub-classes to each of a plurality of pixels of an image of an unknown rock sample ("unknown rock sample image") retrieved from a geological formation, wherein: (1) the ascription utilizes a deep learning model that is trained with an annotated training dataset; and (2) the annotated training dataset comprises: (i) a plurality of multi-pixel images of known rock samples ("known rock sample images"); and (ii) for each known rock sample image, which of the sub-classes corresponds to at least a subset of pixels of that image; (B) for each pixel of the unknown rock sample image having an ascribed sub-class, deriving which one of a plurality of predetermined meta-classes is associated with that pixel based on the sub-class ascribed to that pixel, wherein the meta-classes are each representative of a different one of a plurality of predetermined rock types; and (C) predicting at least one property of the geological formation utilizing the ascription-derived meta-classes, wherein predicting the at least one property includes predicting which one or more of the rock types are present in the geologic formation.

The present disclosure therefore introduces a method to automate the recognition and quantification of rock cuttings using artificial intelligence. The method has been proven with laboratory experiments—controlled environment and process—including that this method could be automated only using RGB low cost photographs. On one side, the subjectivity and the duration of the annotation process is drastically reduced using an image processing algorithm performed on just single lithology photographs. On the other side, the convolutional neural network model and training scheme obtain high accuracy and are robust to different conditions of illuminations, sizes, and rock spatial disposition, for both single and mixed lithology. The model also accurately predicts using wet cuttings, opening the opportunity to remove or at least reduce the duration of the drying process.

The foregoing outlines features of several embodiments so that a person having ordinary skill in the art may better understand the aspects of the present disclosure. A person having ordinary skill in the art should appreciate that they may readily use the present disclosure as a basis for designing or modifying other processes and structures for carrying out the same functions and/or achieving the same benefits of the embodiments introduced herein. A person having ordinary skill in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. § 1.72(b) to permit the reader to quickly ascertain the nature of the technical disclosure. It is submitted with the understanding that it will not be used to interpret or limit the scope or meaning of the claims.

What is claimed is:

1. A method comprising:
    ascribing one of a plurality of predetermined sub-classes to each of a plurality of pixels of an image of an unknown rock sample ("unknown rock sample image") retrieved from a geological formation, wherein:
        the ascription utilizes a deep learning model that is trained with an annotated training dataset; and
        the annotated training dataset comprises:
            a plurality of multi-pixel images of known rock samples ("known rock sample images"); and
            for each known rock sample image, which of the sub-classes corresponds to at least a subset of pixels of that image;
    for each pixel of the unknown rock sample image having an ascribed sub-class, deriving which one of a plurality of predetermined meta-classes is associated with that pixel based on the sub-class ascribed to that pixel, wherein the meta-classes are each representative of a different one of a plurality of predetermined rock types; and
    predicting at least one property of the geological formation utilizing the ascription-derived meta-classes, wherein predicting the at least one property includes:
        predicting which one or more of the rock types are present in the geologic formation; and
        predicting a quantity of each of the one or more rock types predicted to be present in the geologic formation.

2. The method of claim 1 further comprising training the deep learning model with the annotated training dataset.

3. The method of claim 1 wherein the deep learning model includes a convolutional neural network.

4. The method of claim 3 wherein the deep learning model includes nodes each associated with at least a weight, and wherein the training includes optimizing the weights associated to each node using a loss function relative to the annotated training dataset.

5. The method of claim 1 wherein the deep learning model is defined to perform multi-scale processing.

6. The method of claim 1 further comprising defining a plurality of windows in the unknown rock sample image, wherein each window comprises a predetermined number of pixels and is of a predetermined shape, and wherein each known rock sample image of the annotated training dataset comprises the predetermined number of pixels and is of the predetermined shape.

7. The method of claim 1 further comprising:
    forming the annotated training dataset, including:
        obtaining the known rock sample images, wherein the known rock samples depicted in the known rock sample images collectively include one or more known rock types; and
        defining each sub-class via association with at least one subset of pixels of a corresponding one or more of the known rock sample images; and
    associating each defined sub-class to one of the meta-classes that corresponds to the known rock type of the corresponding at least one subset of pixels.

8. The method of claim 7 wherein at least one of the known rock sample images is an image of one of the known rock samples that comprises just one of the known rock types, and wherein the at least one subset of pixels of that image are associated with just one of the sub-classes.

9. The method of claim 1 wherein each sub-class is representative of one or more rock properties.

10. The method of claim 9 wherein the one or more rock properties include one or more of grain size, color, and porosity.

11. The method of claim 10 further comprising predicting one or more of grain size, color, and porosity of the geologic formation based on the ascriptions.

12. The method of claim 1 wherein the known rock sample comprises drill cuttings.

13. The method of claim 12 wherein the unknown rock sample is one of a plurality of unknown rock samples each retrieved from a different depth in the geological formation and depicted in a corresponding one of a plurality of unknown rock sample images, and wherein the method further comprises:
    performing the sub-class ascription, the meta-class derivation, and the at least one property prediction utilizing each of a plurality of unknown rock sample images; and
    generating a lithology profile of the geologic formation versus depth based on the property predictions.

14. The method of claim 1 further comprising:
    collecting a sample of drill cuttings retrieved from a wellbore while drilling into the formation to form the wellbore; and
    via operation of an imaging device, imaging the sample of drill cuttings to obtain the unknown rock sample image.

15. The method of claim 14 wherein parameters of the unknown rock sample image are standardized parameters.

16. The method of claim 15 wherein the standardized parameters include settings of the imaging device operation, including one or more of resolution, brightness, type of support on which the sample of drill cuttings rest during the imaging, and distance between the support and the imaging device.

17. An apparatus comprising:
a processing system comprising a processor and a memory storing an executable computer program code that, when executed by the processor:
ascribes one of a plurality of predetermined sub-classes to each of a plurality of pixels of an image of an unknown rock sample ("unknown rock sample image") retrieved from a geological formation, wherein:
the ascription utilizes a deep learning model that is stored in the memory and that was trained with an annotated training dataset; and
the annotated training dataset comprises:
a plurality of multi-pixel images of known rock samples ("known rock sample images"); and
for each known rock sample image, which of the sub-classes corresponds to at least a subset of pixels of that image;
for each pixel of the unknown rock sample image having an ascribed sub-class, derives which one of a plurality of predetermined meta-classes is associated with that pixel based on the sub-class ascribed to that pixel, wherein the meta-classes are each representative of a different one of a plurality of predetermined rock types; and
predicts at least one property of the geological formation utilizing the ascription-derived meta-classes, wherein the at least one property includes:
which one or more of the rock types are present in the geologic formation; and
a quantity of each of the one or more rock types predicted to be present in the geologic formation.

18. The apparatus of claim 17 further comprising an imaging device for obtaining the unknown rock sample image.

19. A non-transitory, tangible, computer-readable medium having stored thereon computer-readable instructions executable by a processing system for:
ascribing one of a plurality of predetermined sub-classes to each of a plurality of pixels of an image of an unknown rock sample ("unknown rock sample image") retrieved from a geological formation, wherein:
the ascription utilizes a deep learning model that is trained with an annotated training dataset; and
the annotated training dataset comprises:
a plurality of multi-pixel images of known rock samples ("known rock sample images"); and
for each known rock sample image, which of the sub-classes corresponds to at least a subset of pixels of that image;
for each pixel of the unknown rock sample image having an ascribed sub-class, deriving which one of a plurality of predetermined meta-classes is associated with that pixel based on the sub-class ascribed to that pixel, wherein the meta-classes are each representative of a different one of a plurality of predetermined rock types; and
predicting at least one property of the geological formation utilizing the ascription-derived meta-classes, wherein predicting the at least one property includes:
predicting which one or more of the rock types are present in the geologic formation; and
predicting a quantity of each of the one or more rock types predicted to be present in the geologic formation.

20. A method comprising:
ascribing one of a plurality of predetermined sub-classes to each of a plurality of pixels of an image of an unknown rock sample ("unknown rock sample image") retrieved from a geological formation, wherein:
the ascription utilizes a deep learning model that is trained with an annotated training dataset; and
the annotated training dataset comprises:
a plurality of multi-pixel images of known rock samples ("known rock sample images"), wherein the known rock sample comprises drill cuttings; and
for each known rock sample image, which of the sub-classes corresponds to at least a subset of pixels of that image;
for each pixel of the unknown rock sample image having an ascribed sub-class, deriving which one of a plurality of predetermined meta-classes is associated with that pixel based on the sub-class ascribed to that pixel, wherein the meta-classes are each representative of a different one of a plurality of predetermined rock types; and
predicting at least one property of the geological formation utilizing the ascription-derived meta-classes, wherein predicting the at least one property includes predicting which one or more of the rock types are present in the geologic formation;
wherein:
the unknown rock sample is one of a plurality of unknown rock samples each retrieved from a different depth in the geological formation and depicted in a corresponding one of a plurality of unknown rock sample images; and
the method further comprises:
performing the sub-class ascription, the meta-class derivation, and the at least one property prediction utilizing each of the plurality of unknown rock sample images; and
generating a lithology profile of the geologic formation versus depth based on the property predictions.

* * * * *